US006478462B2

(12) United States Patent
Polkus et al.

(10) Patent No.: US 6,478,462 B2
(45) Date of Patent: Nov. 12, 2002

(54) METHODOLOGY FOR DETERMINING X-RAY TO LIGHT FIELD DECENTERING ON DIGITAL RADIOGRAPHIC IMAGE SYSTEMS

(75) Inventors: Vincent S. Polkus, Delafield, WI (US); Robert M. Stetz, Oconomowoc, WI (US); Dale Duemer, Menomonee Falls, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 101 days.

(21) Appl. No.: 09/788,986

(22) Filed: Feb. 20, 2001

(65) Prior Publication Data

US 2002/0114426 A1 Aug. 22, 2002

(51) Int. Cl.[7] .............................................. G01D 18/00
(52) U.S. Cl. ......................... 378/207; 378/205; 378/206
(58) Field of Search ................................ 378/205, 207, 378/163, 166, 206

(56) References Cited

U.S. PATENT DOCUMENTS 6,305,842 B1 * 10/2001 Kunert ........................ 378/147
6,398,408 B1 * 6/2002 Polkus ........................ 378/163
6,402,373 B1 * 6/2002 Polkus et al. ............... 378/207
6,402,374 B1 * 6/2002 Boomgaarden ............. 378/207

* cited by examiner

Primary Examiner—Robert H. Kim
Assistant Examiner—Courtney Thomas
(74) Attorney, Agent, or Firm—Fletcher, Yoder & Van Someren

(57) ABSTRACT

The present technique provides a method and system for centering a radiographic imaging system to provide minimal non-diagnostic radiation to a patient. The present technique incorporates a radio-opaque template that is substantially aligned to a light field produced from a light source. The present technique also incorporates a processing module that determines an offset distance from the features of the template to features detectable in data from an x-ray exposure. A processing module determines the offset distance utilizing an algorithm for recognizing the radio-opaque features and determining distances between the features and the detected edges or similar features of the exposure.

24 Claims, 5 Drawing Sheets

METHODOLOGY FOR DETERMINING X-RAY TO LIGHT FIELD DECENTERING ON DIGITAL RADIOGRAPHIC IMAGE SYSTEMS

FIELD OF THE INVENTION

The present invention relates generally to digital imaging systems. Particularly, the present invention relates to an edge and pattern recognition technique for x-ray to light field alignment in digital radiographic image systems.

BACKGROUND OF THE INVENTION

Digital x-ray imaging systems are becoming increasingly widespread for producing digital data, which can be reconstructed into useful images. In current digital x-ray imaging systems, radiation from an x-ray source is directed toward a subject, typically a patient in a medical diagnostic application. A portion of the radiation passes through the patient and impacts a detector. The surface of the detector converts the radiation to light photons, which are sensed. The detector is divided into a matrix of discrete picture elements or pixels, and encodes output signals based upon the quantity or intensity of the radiation impacting each pixel region. Because the radiation intensity is altered as the radiation passes through the patient, the images reconstructed based upon the output signals provide a projection of the patient's tissues similar to those available through conventional photographic film techniques.

In available digital detectors, the surface of the detector is divided into a matrix of picture elements or pixels, with rows and columns of pixels being organized adjacent to one another to form the overall image area. When the detector is exposed to radiation, photons impact a scintillator coextensive with the image area. A series of detector elements are formed at row and column crossing points, each crossing point corresponding to a pixel making up the image matrix. In one type of detector, each element consists of a photo-diode and a thin film transistor. The cathode of the diode is connected to the source of the transistor, and the anodes of all diodes are connected to a negative bias voltage. The gates of the transistors in a row are connected together and the row electrode is connected to scanning electronics. The drains of the transistors in each column are connected together and each column electrode is connected to additional readout electronics. Sequential scanning of the rows and columns permits the system to acquire the entire array or matrix of signals for subsequent signal processing and display.

In use, the signals generated at the pixel locations of the detector are sampled and digitized. The digital values are transmitted to processing circuitry where they are filtered, scaled, and further processed to produce an image data set. The image data set may then be used to store the resulting image, to display the image, such as on a computer monitor, to transfer the image to conventional photographic film, and so forth. In the medical imaging field, such images are used by attending physicians and radiologists in evaluating the physical conditions of a patient and diagnosing disease and trauma.

The installation and setup procedures for digital imaging systems, such as radiographic diagnostic imaging systems, can be complex and time-consuming. For example, to comply with customer image quality and consistency requirements and various regulatory and safety standards for diagnostic imaging systems, such procedures generally require the determination of a variety of factors, including the accurate positioning of the x-ray source with respect to the x-ray detector. Additionally, the determination of the separation distance between the x-ray source and x-ray detector, referred to as the source-to-image distance (SID), must also be established. Moreover, the setup generally requires that the x-ray field produced by the source be accurately positioned to avoid excessive exposure to radiation and the possible need to retake desired exposures.

To minimize the administration of non-diagnostic radiation to human patients, it is desirable to control and limit x-ray exposure that is unnecessary for creating the image data set. Hospitals typically control and limit x-ray exposure by conforming to regulatory standards. For instance, on radiographic systems, a visible light beam is often used by the operator to position the diagnostic x-ray source assembly with respect to the patient. Regulatory standards limit allowable misalignment between the projected visible light and radiation fields to ensure delivery of x-rays to the desired area. These standards generally restrict the total misalignment of the four edges of the projected rectangular field to a stated percentage of the source to image distance (SID).

United States Department of Health and Human Services criteria restrict the misalignment of the light and x-ray beams to be less than 2% of the indicated SID for the system. Users, typically, perform testing and record the results for each system prior to turnover of the system for diagnostic use and periodically in accordance with a quality assurance processes thereafter during the lifecycle of the system.

In a conventional field alignment test, the edges of the light field are located using some type of visible/radio-opaque tool to mark the position. Next, an x-ray exposure is taken and the physical edges of the radiation field are measured in relationship to the corresponding light-field marks on the resulting image. This process is manual and inexact, and therefore is characterized by high statistical variance. Because of the error associated with the measurement process, it is necessary to set internal rejection limits significantly below the limits mandated by the regulatory agencies. In cases where systems exceed the rejection limit, it is necessary to readjust the diagnostic source assembly, reposition the collimator or light bulb, and then retest to confirm compliance with the centering criteria.

There is need, therefore, for a novel technique, for determining radiation field to light field decentering on digital radiographic image systems.

SUMMARY OF THE INVENTION

The invention provides a novel technique for x-ray field alignment designed to respond to such needs. The technique utilizes a radio-opaque template with unique geometric features and attributes that are subsequently projected onto a digital detector by means of radiographic imaging and subsequently analyzed in a manner that automates the computation of the x-ray to light field misalignment. The technique includes a method for calibrating an imaging system. The method includes positioning an x-ray source to generate an x-ray beam at a detector. The method also includes directing a light beam at the director where a light field is produced and provides the area which the radiographic template is aligned. The x-ray field is then compared to the aligned template and the distances between the peripheral edges of the radiation field and the template are calculated. Once the distances are computed to determine the location of the vertices of the radio-opaque pattern, the offset distance is computed. The radiation field is aligned with the light field, providing a predictable exposure area and reducing the amount of non-diagnostic radiation delivered to a patient.

DETAILED DESCRIPTION OF THE INVENTION

Figure 1:
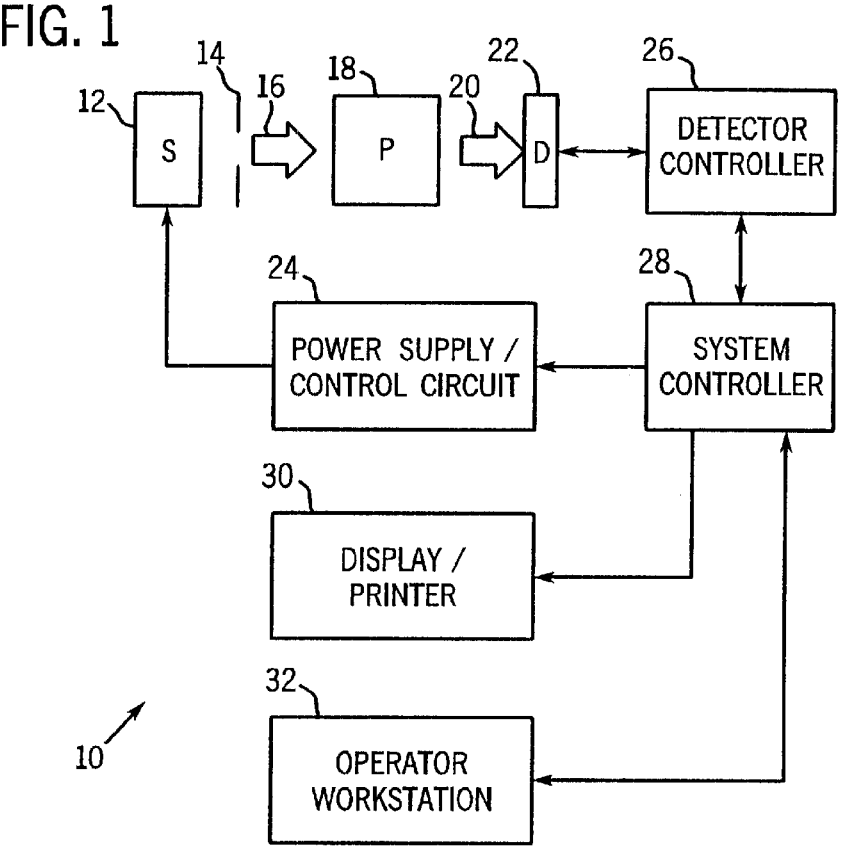
FIG. 1 is a diagrammatical overview of an exemplary imaging system, in the illustrated example a digital x-ray imaging system, in which the present technique is incorporated.

FIG. 1 illustrates diagrammatically an imaging system 10 for acquiring and processing discrete pixel image data. In the illustrated embodiment, system 10 is a digital x-ray system designed both to acquire original image data, and to process the image data for display in accordance with the present technique. Particularly, system 10 is a digital x-ray system that facilitates installation and calibration procedures such that accurate image can subsequently be acquired and processed by the system 10 for output and display. In the embodiment illustrated in FIG. 1, imaging system 10 includes a source of x-ray radiation 12 positioned adjacent to a collimator 14. Collimator 14 permits a stream of radiation 16 to pass into a region in which a subject, such as a human patient 18 is positioned. It should be understood that the stream of radiation generally passes through an opening 15 in the collimator 14. Opening 15 in collimator 14 is adjustable such that the stream of radiation 16 may be varied. A portion of the radiation 20 passes through or around the subject and impacts a digital x-ray detector, represented generally at reference numeral 22. As described more fully below, detector 22 converts the x-ray photons received on its surface to lower energy photons, and subsequently to electric signals, which are acquired and processed to reconstruct an image of the features within the subject.

Source 12 is controlled by a power supply/control circuit 24 which furnishes both power and control signals for examination sequences. Moreover, detector 22 is coupled to a detector controller 26 which commands acquisition of the signals generated in the detector. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be noted that the present invention may also incorporate a processing module, which automatically calibrates the imaging system according to specifications. Further, the processing module may be utilized to determine the distance from the source 12 to the detector 22 or source to image distance (SID) and to determine the alignment of light and x-ray fields, which may be computed on the basis of the SID. It should be further noted that the processing module may also compute the offset values for the light and x-ray fields determined by algorithms described more fully below.

Figure 2:
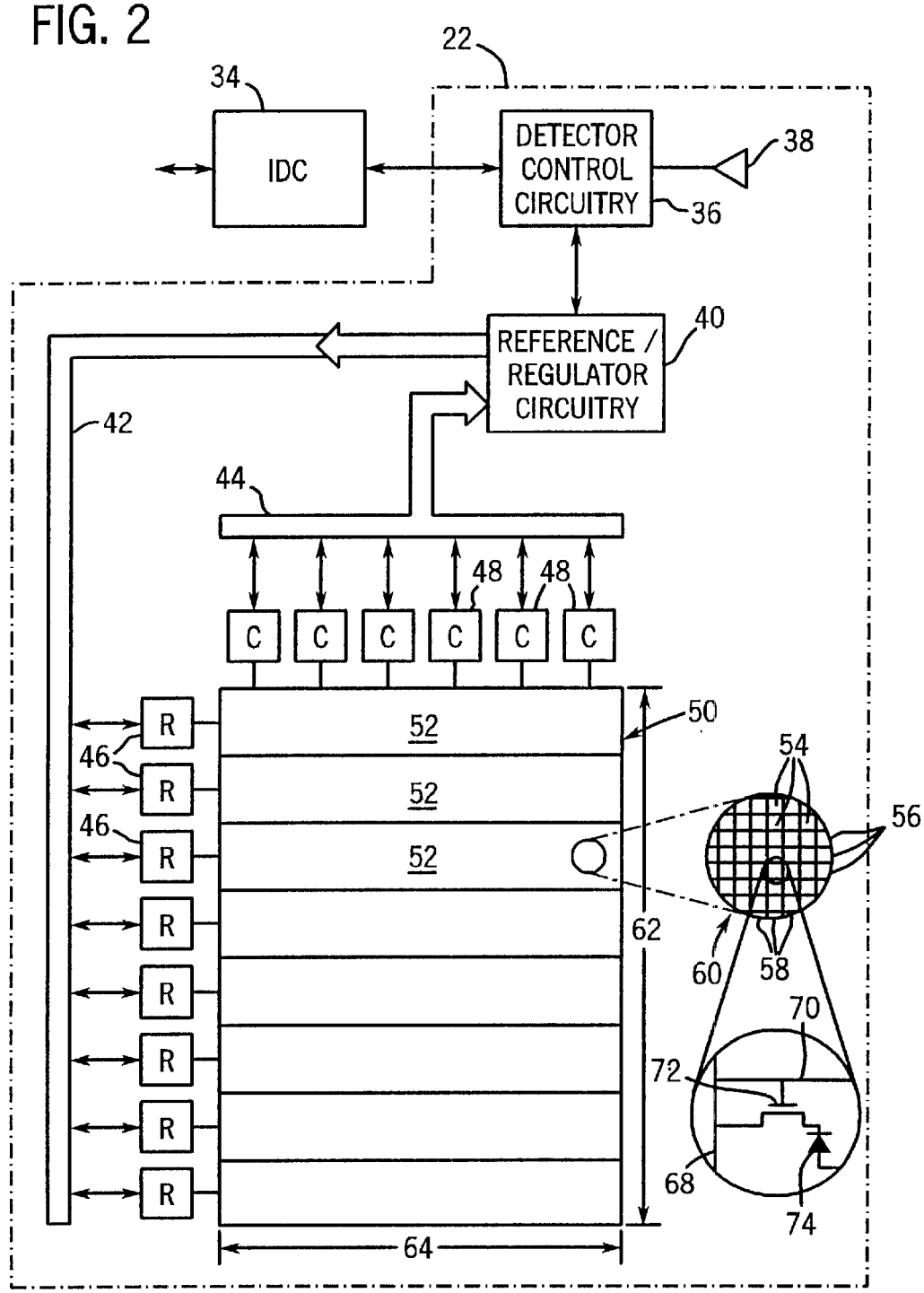
FIG. 2 is a diagrammatical representation of certain of the functional circuitry for producing image data in the system of FIG. 1.

FIG. 2 is a diagrammatical representation of functional components of the digital detector 22. FIG. 2 also represents an imaging detector controller or IDC 34, which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40, and receives digital image pixel data from circuitry 40.

In the present illustrated embodiment, detector 22 consists of a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32 following reconstruction of the image. Thus, in the present technique, readout electronics can provide the processing module data regarding the location and intensity of the detected image edges. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the particular embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46, and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Figure 3:
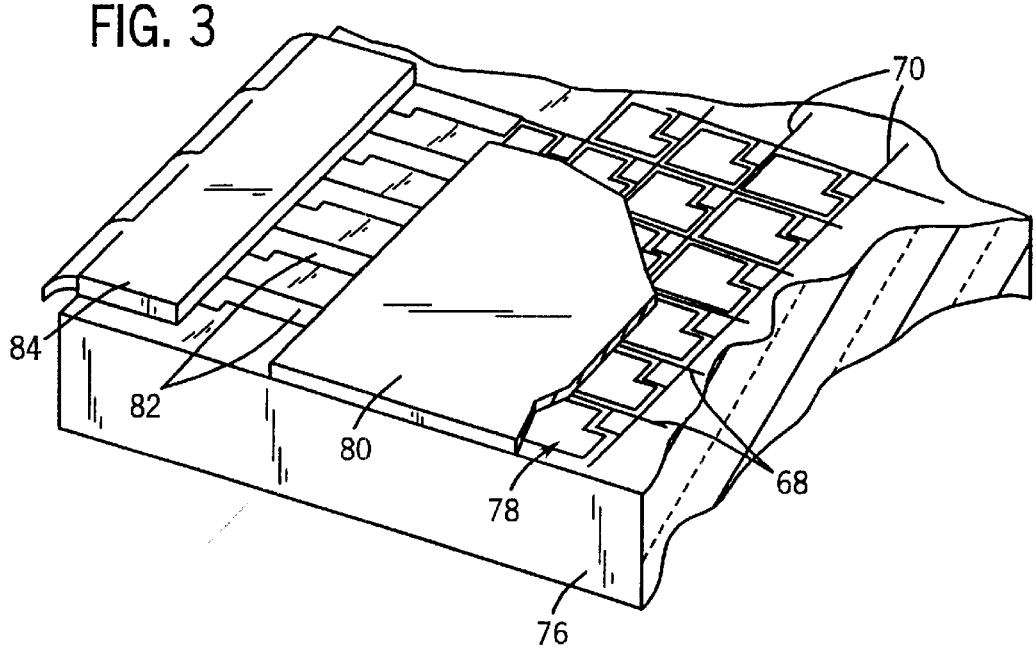
FIG. 3 is a partial sectional view illustrating an exemplary detector structure for producing the image data.

FIG. 3 generally represents an exemplary physical arrangement of the components illustrated diagrammatically in FIG. 2. As shown in FIG. 3, the detector may include a glass substrate 76 on which the components described below are disposed. Column electrodes 68 and row electrodes 70 are provided on the substrate, and an amorphous silicon flat panel array 78 is defined, including the thin film transistors and photodiodes described above. A scintillator 80 is provided over the amorphous silicon array for receiving radiation during examination sequences as described above. Contact fingers 82 are formed for communicating signals to and from the column and row electrodes, and contact leads 84 are provided for communicating the signals between the contact fingers and external circuitry. In the present embodiment, a radiographic template (not shown) may be disposed on the detector 22. The radiographic template will be discussed further below in greater detail.

Before imaging system 10 may be used to perform examination sequences, system 10 is properly installed and calibrated to ensure compliance with customer needs, performance requirements, and various regulatory standards. A performance variable established during the setup and calibration process is the proper alignment of the x-ray field produced by the x-ray source. In an exemplary implementation, this alignment may be expressed as a function of the system SID setting, which may also be calibrated in the set up procedure.

Figure 4:
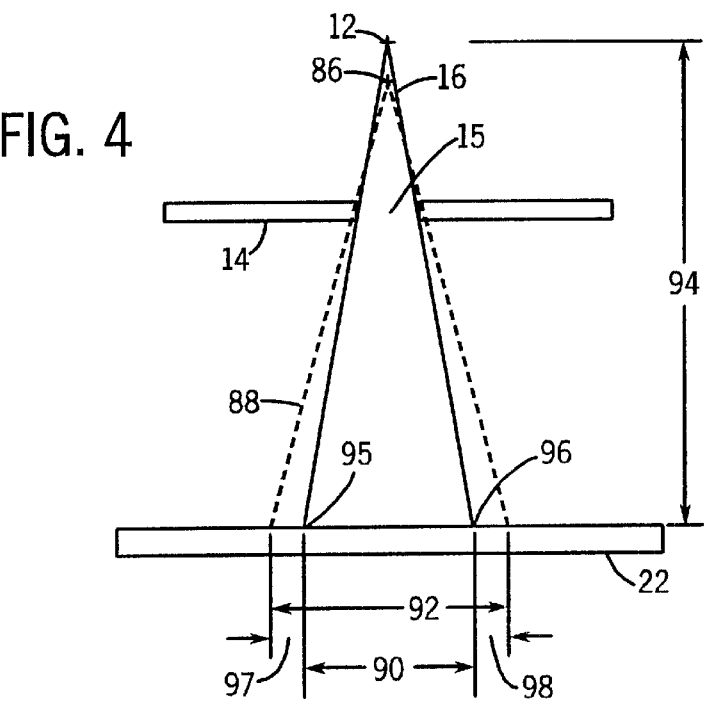
FIG. 4 is an exemplary technique for setup and calibration of a digital x-ray imaging system of FIG. 1.

Turning now to FIG. 4, an exemplary technique for centering a radiographic imaging system 10 is illustrated. The technique illustrated in FIG. 4 can be used alone or in conjunction with other techniques and will be explained more fully below. An x-ray source 12 is shown emitting a stream of radiation or an x-ray beam 16 passing through collimator 14 and opening 15, and creating a radiation field on the detector 22. A light source 86 is also illustrated emitting a light beam 88 through collimator 14 and opening 15, forming a light field on the detector 22.

Detector 22 detects the impact of the x-ray beam 16 on an area referenced by numeral 90 and generates electrical signals representative of the detected beam. Similarly, the light source 86 produces a light field on an area 92 with visible peripheral edges. In the present centering technique, the peripheral edges of the light field are utilized as a marking tool for a radio-opaque template (not shown in FIG. 4). The radio-opaque template and its use in aligning the light and x-ray fields will be discussed further below.

Reference numeral 94 represents the separation distance from the detector to the x-ray source, or SID. It may also be pointed out that x-ray beam 16 and light beam 88 have beam angles, which may be determined by the size of the opening 15. The beam angles and the opening 15 may be used to define the radiation field area 90 and light field area 92. As mentioned above, detector 22 detects the impact of x-ray beam 16 and generates electrical signals. Based on these electrical signals the size of the radiation area 90 may be determined by detector controller 26 and system controller 28. The radiation field area 90 is illustrated with peripheral edges 95 and 96. Further, reference numerals 97 and 98 represent the offset or misalignment between the detected peripheral edges 95 and 96 of the radiation field to the detected peripheral edges of the light field. The radio-opaque template provides the location of the edges of the light field and the method in which it is utilized to measure the offsets 97 and 98 will be discussed more fully below. Lastly, although detector 22 is shown in a horizontal position, the exemplary technique applies also to upright detectors and to systems capable of various angular orientations of the source and detector.

Figure 5:
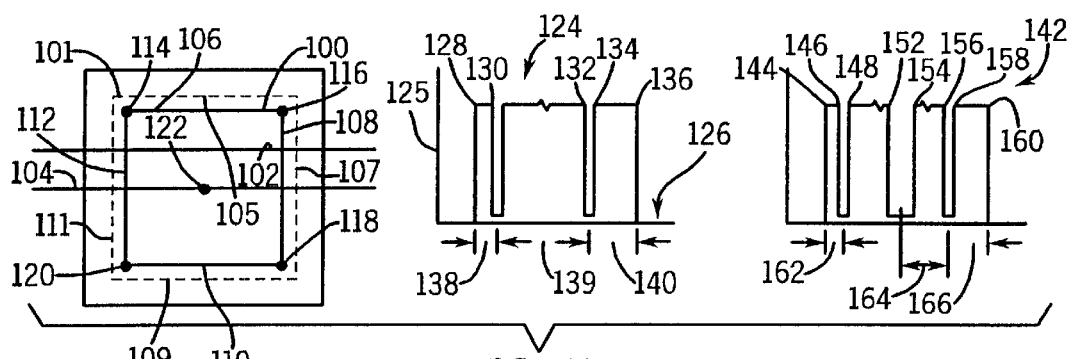
FIG. 5 illustrates a radio-opaque template and edges of the x-ray exposure and corresponding histograms depicting the intensity levels with respect to the pixel location when two edges of the exposure are detected.

FIG. 5 illustrates a radio-opaque template 100 located generally on or adjacent to the detector 22. However, it should be noted that the template 100 may be placed on a patient support surface or even directly in contact with the radiographic grid (not shown). The radio-opaque template 100 is shown in a rectangular or square geometrical shape and placed on the detector 22. It should be further noted that the shape of the template 100 may be in any geometrical shape. Thus, as the light beam 86 is generated, the template 100 is positioned so that the peripheral edges of the light field are substantially parallel to and coincident with features of the template, such as the defined edges.

FIG. 5 more specifically represents a centering technique illustrating the pattern of the radio-opaque template 100 and the detected radiation field or exposure area 101. Section lines 102 and 104 illustrate the cross sectional pixel analysis of the detected exposure area 101 on the detector 22 with respect to the radio-opaque template 100. The radio-opaque template 100 generally has four radio-opaque lines as referenced by numerals 106, 108, 110, and 112. In an exemplary implementation, the template is made of a sheet of plastic, such as clear Plexiglas, while the lines formed on the template are made of metal wire. The x-ray image exposure area 101 is illustrated with peripheral edges 105, 107, 109, and 111. The radio-opaque template 100 also contains a plurality of radio-opaque points as referenced by numerals 114, 116, 118, and 120, conveniently located at four vertices. The radio-opaque points may be made of any suitable material, such as phosphorous. Where desired, additional points may be provided for computation of decentering or offset as described below. In the embodiment of FIG. 5, for example a radio-opaque point 122 is located at the center of the template. Other additional radio-opaque points on the template may be used to provide additional bases for calculating the offset distances, as discussed in more detail further below.

FIG. 5 also illustrates histograms that provide a graphical representation of the intensity of x-ray radiation measured with respect to the location on the area detected. Particularly, the histograms represent a technique utilized to compute the effective row and column locations where the x-ray field impacts the template 101, as indicated by the intensity effects of the radio-opaque lines and points. More particularly, FIG. 5 represents a test exposure when the radio-opaque pattern has been imaged by the detector 22.

The intensity profile across the detector area along line 102 is illustrated by histogram 124. The horizontal axis of the histogram 124 represents the row (or column, depending upon the frame of reference) number or location on the detector 22, and the vertical axis 125 represents the level of intensity detected with respect to the location. It should be noted that the intensity level drops off, and is illustrated as low where the incident x-ray radiation encounters radio-opaque components of the template or when the exposure 101 is no longer detected by the readout electronics (i.e. at edges of the exposure area). Reference numeral 128 indicates the location at which the peripheral edge 111 of the exposure 101 is detected. The intensity of the image exposure 101 remains high until line 102 crosses the radio-opaque line 112, as referenced by numeral 130. On an opposite side of the radio-opaque line of the template, a high intensity level is illustrated until line 102 crosses the template line 108, as referenced by numeral 132. Reference numeral 134 represents a position at an opposite side of line 108 where the detector again reads a high intensity. Reference numeral 136 represents the position at which the exposure 101 is no longer detected (i.e. the right edge of the exposure area in the illustrated implementation). It should be noted that the distance from peripheral edge 111 of the exposure area to the first radio-opaque line 112 is referenced by numeral 138. Reference numeral 140 represents the distance from the radio-opaque line 108 to the opposite peripheral edge 107 of the image exposure area 101.

Histogram 142 similarly represents the detection of the image exposure area 101 with respect to the radio-opaque template 100 along line 104. Reference numeral 144 illustrates a high intensity at a position when peripheral edge 111 of the exposure area 101 is detected along line 104. At reference numeral 146 the radio-opaque line 112 is detected as illustrated by a drop in intensity. The intensity level then rises again, as referenced by numeral 148, on an opposite side of the line, and continues at an elevated level until radio-opaque point 122 is crossed by line 104. The point produces a drop in intensity as referenced by numeral 152. Reference numeral 154 represents the rise in intensity on an opposite side of the point. The intensity remains elevated until the radio-opaque line 108 is detected, as referenced by numeral 156. At reference numeral 158, the intensity level of the image once again rises at the opposite side of the line, and remains high until peripheral edge 107 of image exposure area 101 is crossed, as referenced by numeral 160.

Reference numeral 162 represents the distance from the peripheral edge 111 of the image exposure area 101 to the radio-opaque edge 112. Reference numeral 164 represents the distance from the radio-opaque point 122 to the line 108 of the radio-opaque template. Lastly, reference numeral 166 refers to the distance from the radio-opaque line 108 to the peripheral edge 107 of the image exposure area 101.

The distances mentioned above are utilized in the calibration procedure described further below. It should be understood that FIG. 5 illustrates a detection scheme wherein the entire image exposure area 101 is detected. Furthermore, calibration of the system 10 may include reducing the area of the radiation field. The radio-opaque template 100 provides the location where an optimal area for radiation may be directed to facilitate the calibration of the system 10. This may include increasing or reducing the area of the radiation field to equal the area covered by the radio-opaque template. In particular, as described below, the light field may be used as a basis for aligning the template, such as by positioning the lines or other indicia of the template with the light field. The subsequent x-ray exposure provides an actual indication of the region where the x-ray field is incident and, thereby, an indication of the relative offset or inaccuracy in positioning of the light and x-ray fields.

Figure 6:
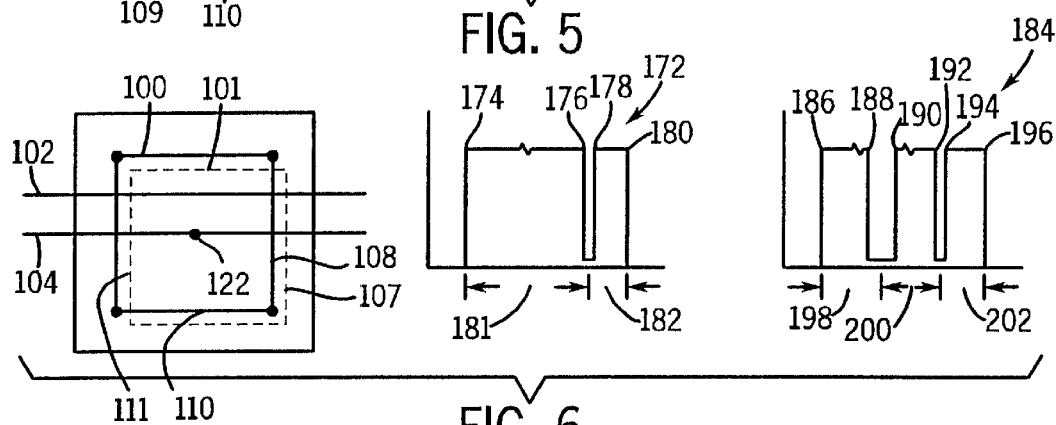
FIG. 6 illustrates a radio-opaque template and edges of the x-ray exposure and corresponding histograms depicting the intensity levels with respect to the pixel location when one edge of the exposure is detected.

Turning to FIG. 6, another embodiment is illustrated showing an exposure area 101 of an image wherein only two lines 108 and 110 of the radio-opaque template 10 are detected along lines 102 and 104. Histogram 172 illustrates graphically the detection of the radiation field with respect to the radio-opaque template on the detector 22. Specifically, reference numeral 174 illustrates a position at image exposure edge 111. The intensity of the received radiation remains elevated until the radio-opaque line 108 is detected as illustrated by reference numeral 176. At reference numeral 178, the opposite side of the line 108 is detected, and the intensity level remains elevated until peripheral edge 107 of the image exposure area 101, as referenced by numeral 180. The distance from the peripheral edge 111 of the image exposure area 101 to the radio-opaque line 108 is referenced by numeral 181. The distance from the radio-opaque line 108 to the peripheral edge 107 of the image exposure area 101 is referenced by numeral 182.

Histogram 184 illustrates the detection of the exposure as referenced by line 104. Reference numeral 186 represents the location where peripheral edge 111 of the image exposure area 101 is detected. The intensity level thereafter remains elevated until radio-opaque point 122 is detected, as referenced by numeral 188. At reference numeral 190, the opposite side of the point is encountered, resulting in a rise in intensity level until the radio-opaque line 108 is detected at reference numeral 192. At reference numeral 194, the opposite side of the line is detected, and the intensity remains elevated until peripheral edge 107 of the exposure area 101, as referenced by numeral 196.

The distance from peripheral edge 111 of the image exposure area to the position at which the radio-opaque line 108 is detected is referenced by numeral 198. The distance from the radio-opaque point 122 to the radio-opaque line 108 is referenced by numeral 200. Reference numeral 202 represents the distance from the radio-opaque line 108 to the peripheral edge 107 of the image exposure area 101 is referenced by numeral 196.

As described below, the offset distance for calibrating the scheme illustrated in FIG. 6 may be calculated by comparing the distances from the radio-opaque lines and the detected edges of the image exposure area 101. It should be understood that the template location in known due to its positioning based upon the visible light field, and therefore once the distances are calculated by the system, the calibration procedure becomes relatively straightforward.

Figure 7:
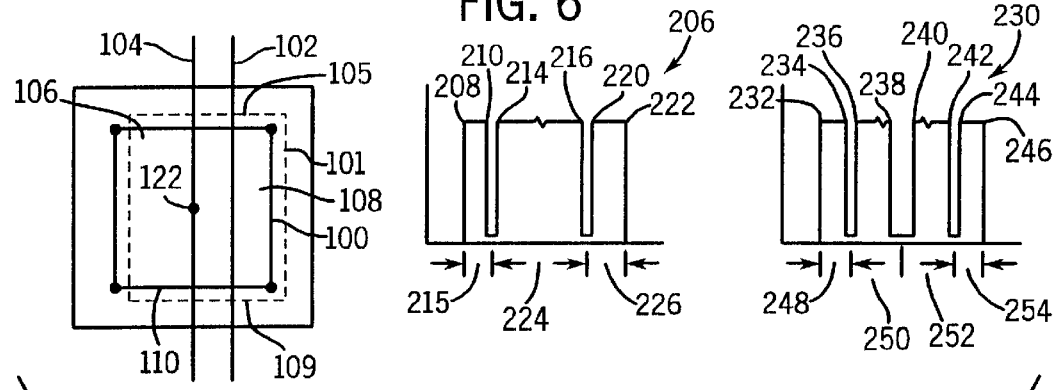
FIG. 7 illustrates a radio-opaque template and edges of the x-ray exposure and corresponding histograms depicting the intensity levels with respect to pixel location when three edges of the exposure are detected.

FIG. 7 illustrates yet another scenario wherein the detector detects an image exposure area 101 in which three edges 106, 108, 110 of the radio-opaque template are detected. Lines 102 and 104 are illustrated as vertical section lines rather than horizontal section lines as in the scenarios set forth above. Histograms 206 and 230 represent the intensity level of the resulting exposure with respect to locations along lines 102 and 104, respectively. At reference numeral 208, the peripheral edge 105 of the image exposure area 101 is detected along line 102. At reference numeral 210, the radio-opaque line 106 is detected and the intensity level is shown dropping until the opposite side of the line is detected as referenced by numeral 214. It should be noted that the distance from the peripheral edge 105 of the image exposure area 101 and the radio-opaque line 106 is referenced by 215. The intensity level remains high across the image exposure area 101 until the radio-opaque template line 110 is detected, as referenced by numeral 216. At reference numeral 220, the opposite side of the line is detected and thereafter the intensity remains high until peripheral edge 109 of image exposure area 101, as referenced by numeral 222. Reference numeral 224 indicates the distance from radio-opaque line 106 to radio-opaque line 110. The distance from radio-opaque line 110 to the peripheral edge 109 of the image exposure area 101 is referenced by numeral 226.

Histogram 230 illustrates the intensity levels across the image exposure 101 along line 104. It should be mentioned again that the horizontal axis represents the location, whereas the vertical axis represents the level of intensity. Reference numeral 232 refers to the detection of exposure area 101 at peripheral edge 105. At reference numeral 234, the radio-opaque line 106 is detected and the intensity is shown as low until the opposite side of the line as referenced by numeral 236. The intensity across the image exposure area 101 remains high until radio-opaque point 122 is crossed by line 104, at which point the intensity drops as referenced by numeral 238. The intensity remains low until the opposite side of the point is encountered as referenced by numeral 240. The intensity then rises and continues to be elevated until radio-opaque line 110 is detected at reference numeral 242. The opposite side of the line results in a rise in the intensity level at reference numeral 244, from which point the intensity remains high until the peripheral edge 105 as referenced by numeral 246.

The distance from peripheral edge of the exposed image area 101 to the radio-opaque edge 106 is referenced by numeral 248. The distance from radio-opaque line 106 to radio-opaque point 122 is referenced by numeral 250, and reference numeral 252 represents the distance from the radio-opaque point 122 to radio-opaque line 110. Finally, the distance from radio-opaque line 110 to the peripheral edge 109 of the image exposure area 101 is referenced by numeral 254.

Figure 8:
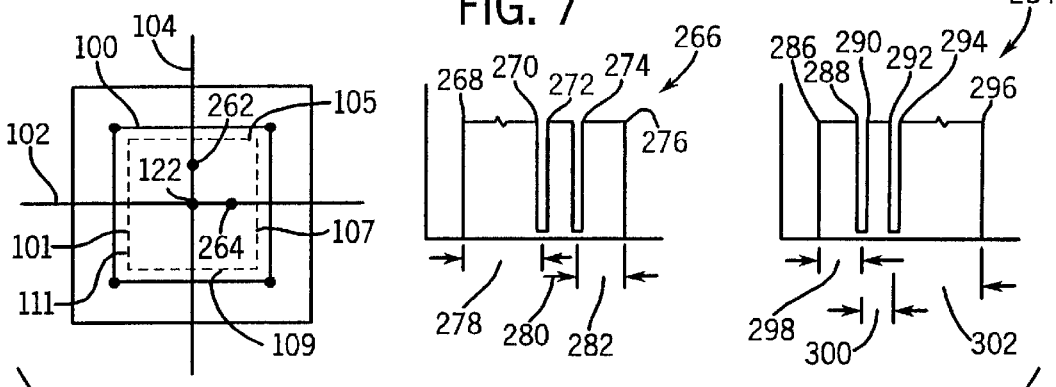
FIG. 8 illustrates a radio-opaque template and edges of the x-ray exposure and corresponding histograms depicting the intensity levels with respect to pixel location when no edges are detected.

FIG. 8 illustrates another embodiment of the present technique wherein the image exposure area 101 lies fully within all radio-opaque lines 104, 106, 110, 112. To accommodate such scenarios, radio-opaque points 122, 262, and 264 are provided. Histogram 266 illustrates the intensity levels along a line 102. Reference numeral 268 indicates the point at which the peripheral edge of the image exposure area 111 is detected as shown by a high intensity level that continues until radio-opaque point 122 is detected at reference numeral 270. On an opposite side of this point, as referenced by numeral 272, the intensity returns to a high level until radio-opaque point 264 is detected at which point the intensity level drops, as referenced by numeral 274. The intensity then rises again on an opposite side of the radio-opaque point 264, after which the intensity remains high until the peripheral edge 107 of the image exposure area 101 as illustrated by reference numeral 276.

The distance from the detected peripheral edge 111 to the radio-opaque point 122 is referenced by numeral 278. Further, the distance from radio-opaque point 122 to radio-opaque point 264 is illustrated by reference numeral 280. Reference numeral 282 represents the distance from radio-opaque point 264 to peripheral edge 107 of the image exposure area 101.

Histogram 284 represents intensity levels across the detector 22 along line 104. Reference numeral 286 indicates the detection of the edge 105 of the image exposure area 101. The intensity level remains high until radio-opaque point 262 is detected as referenced by numeral 288. At an opposite side of the point, the intensity again rises, as represented by numeral 209 until radio-opaque point 122 is detected along line 104, as represented by numeral 292. At an opposite side of this point, the intensity level rises and remains high, as represented by reference numeral 292 until peripheral edge 109, as referenced by numeral 296.

Reference numeral 298 represents the distance from the peripheral edge 105 of the detected image to the radio-opaque point 262. The distance from radio-opaque point 262 to radio-opaque point 122 is referenced by numeral 300, and the distance from radio-opaque point 122 to peripheral edge 109 of the image exposure area 101 is referenced by numeral 302.

The various alignment scenarios depicted in FIGS. 5, 6, 7 and 8 allow for detection of offsets between the light field with which the radio-opaque template is positioned and the actual boundaries of incidence of the x-ray field. Moreover, as described below, the use of a digital detector allows for automation of the alignment offset detection process by permitting rapid and accurate analysis of the locations (rows and columns) of the features of the template, including the lines and points in the illustrated implementation.

Figure 9:
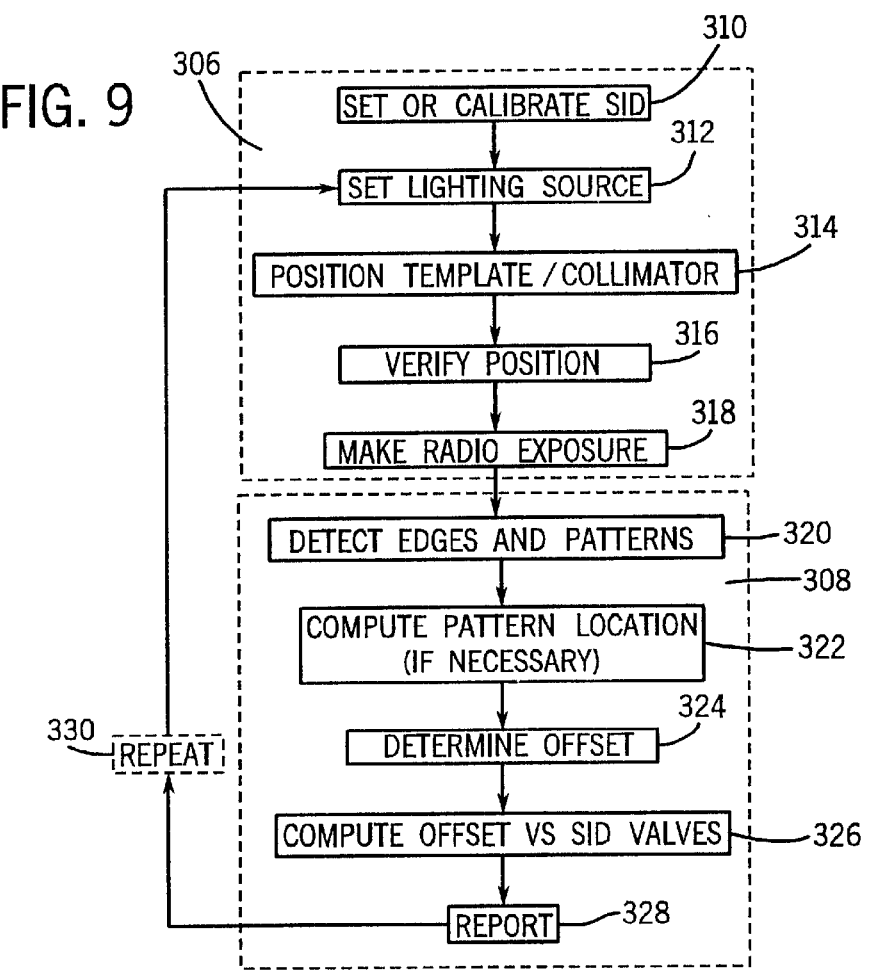
FIG. 9 is a flow chart illustrating an exemplary method for determining x-ray to light field decentering on digital radiographic image systems.

FIG. 9 is a flowchart representing a method for calibrating the imaging system 10. Sequence 306 represents the initial setup procedures for implementing the present technique. Sequence 308 represents an exemplary algorithm and computation approach employed to complete the technique described. The initial step in the method for computing the offset distance of the exposure is to set or calibrate the source-to-image distance (SID) as represented by step 310. Once the source-to-image distance (SID) is calibrated or set according to operator specifications, the light source is set as referenced by step 312. Once the light source is calibrated, the radiographic template is positioned upon the detector as indicated by step 314. The template is set so that the edges of the template are substantially the same as the edges of the light field. As will be appreciated by those skilled in the art, any suitable alignment or positioning approach may be adopted at this step, including positioning with respect to other types of markings. Once the source-to-image distance (SID), the light source, template, and the collimator are set, the positions are verified as indicated by step 316. With all of the positions having been verified, a radiographic exposure is generated as indicated by step 318. It should be understood that the light beam produced by the light source provides the exact position where the radiographic template may be positioned.

Once the exposure is taken, the radiographic pattern is detected by the readout electronics of the detector 22 as indicated by step 320. From this image data, the peripheral edges of the image exposure are detected, as are the radio-opaque features of the template lying within the exposure area. A mathematical computation is performed to determine the pattern location as indicated by step 322. Next, an algorithm is utilize d to deter mine the offset value as indicated by step 322. In a present algorithm, the offset value is the difference in distance from the light field to the radiation field. The light field is typically the area where non-diagnostic radiation is minimal. Therefore, the offset value is computed so that the system 10 may be calibrated with respect to the SID value as indicated by step 326. Finally, at step 328 the values are reported to an operator or a processing module. The procedure may be repeated as indicated by step 330, such as by resetting or repositioning the light source according to new standards or as a function of the results of the previous measurements, as referenced by step 312.

Figure 10:
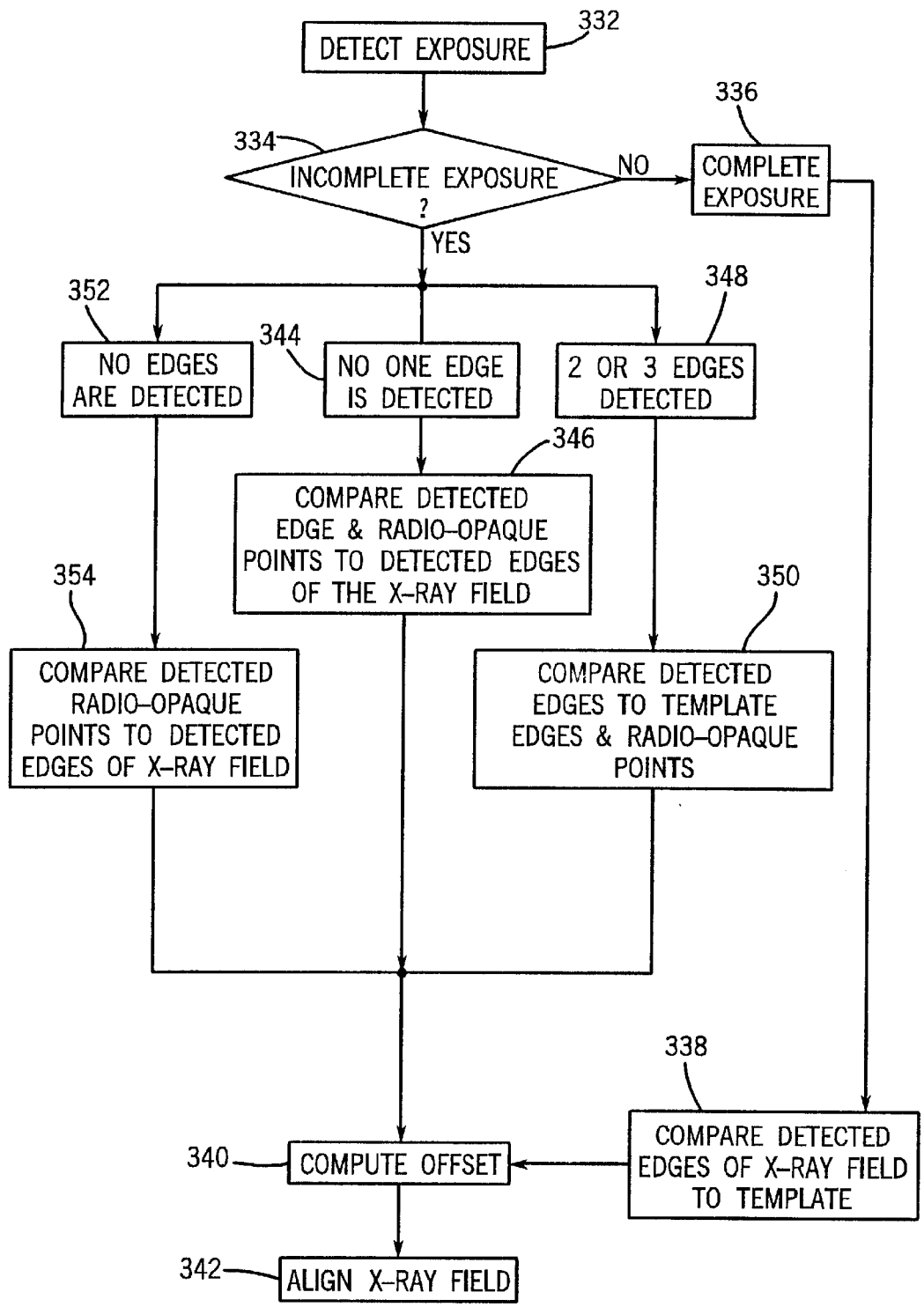
FIG. 10 is a flow chart illustrating the use of an algorithm for determining x-ray to light field decentering on digital radiographic image systems.

FIG. 10 is a flowchart representing a method for calibrating a radiographic imaging system. Initially, an x-ray exposure is detected by the detector as indicated by step 332. Once the x-ray exposure is detected, a processing module determines whether the exposure is incomplete as indicated by step 334. Specifically, the technique utilizes an algorithm to determine whether or not the entire radio-opaque pattern has been completely imaged. The algorithm concludes that the pattern has been completely images if all four coners of the pattern have been sensed in the detected exposure. Thus, if a complete image exposure is detected, as indicated by step 336, the processing module receives data regarding the location of the detected edges of the exposure and the peripheral edges of the radiographic template. FIG. 5 illustrates the situation when a complete exposure is detected. The processing module compares the distances from the radio-graphic lines 108, 112 and point 122 with peripheral edges 109, 111 to determine the offset value as indicated by step 338 and step 340. Once the offset value is calculated, the x-ray field is aligned accordingly, as indicated by step 342. It should be noted that similar analysis may be performed in an opposite direction so as to provide indications of offsets on all sides of the exposure area.

If the exposure is incomplete, and if only one edge is detected as indicated by step 344, the processing module compares the detected edge to the radio-opaque lines and points to determine the offset value as indicated at step 346 in FIG. 10. It should be noted that if fewer than four corners are detected, the system may perform intermediate calculations to estimate the locations of the sides or corners of the radio-opaque template based on known actual sizes of the template features and the distances between them. Once the data is collected and compared, the offset distances can be computed as indicated by step 340. Based upon the offsets the x-ray imaging system 10 may be aligned accordingly, if required, as suggested by step 342.

FIGS. 6 and 7 illustrate scenarios in which two and three lines of the template are detected, respectively, as indicated by step 348 in FIG. 10. When two are three edges are detected, the system establishes the row and column coordinates of the recorded vertices or lines, as well as of the other detected features of the template. Next, the known separation distances between the features, are used to approximate the coordinates of the missing vertices. The distances are used to compute the offset values as indicated by step 340. Once the offset values are calculated, the system is aligned accordingly, if required, as indicated by step 342.

In another test exposure as illustrated in FIG. 8, no lines of the template are detected as in step 352 of FIG. 10. In such cases, other features, such as the radio-opaque points of the template may be used to determine the offset distances as indicated by step 354. As mentioned above, the system uses an algorithm to determine the relative position of the vertices by approximating the coordinates. Particularly, the distances between the peripheral edges of the exposure and the radio-opaque points are used to determine the coordinates of the vertices or lines, as the distances between these features are known in advance. Thus, reconstruction of the light field coordinates is accomplished using the known separation distance to the auxiliary points 262 and 264 in the example of FIG. 8, as well as recognition of the orientation vector that serves to direct the algorithm to the unique set of vertices. Once the distances are computed and compared to the edges of the exposure, the offset values can be determined. Thus, the system can be accordingly aligned as desired, therefore minimizing the non-diagnostic radiation supplied to the patient as indicated by steps 340 and 342. It should be noted that the regulatory testing for the system as described above can be done in an automated and consistent manner relative to the current technique that involves direct measurement by an operator.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for calibrating an imaging system, the method comprising the acts of:

positioning an x-ray source configured to generate a first x-ray beam at a distance from a digital detector;

positioning a light source at a distance from the digital detector;

generating a light field in a first area on the digital detector;

generating an x-ray field in a second area on the digital detector; and computing a separation distance between the first area and the second area.

2. The method as in claim 1, wherein a radio-opaque template is adapted to the digital detector and positioned on the detector for identifying the first area.

3. The method as in claim 2, wherein the radio-opaque template comprises a plurality of radio-opaque lines and points.

4. The method as in claim 2, wherein the lines of the radio-opaque template are substantially parallel to and coincident with the light field.

5. The method as in claim 1, wherein the digital detector comprises a plurality of rows and a plurality of columns which define an image matrix, and wherein the method includes detecting the lateral peripheral edges of the x-ray field via the rows and columns of the matrix.

6. The method as in claim 3, wherein computing the separation distance further comprises:

determining a distance from at least one peripheral line of the radio-opaque template to a peripheral edges of the x-ray field; and determining a distance from the radio-opaque points to the peripheral edges of the x-ray field.

7. The method as in claim 2, wherein aligning the x-ray source further comprises determining an offset distance between the light field and the x-ray field.

8. The method as in claim 7, wherein aligning the x-ray source further comprises shifting the x-ray source by an offset distance to center the x-ray field with the radio-opaque template.

9. A digital radiographic imaging system, comprising:

a digital x-ray detector;

an x-ray source configured to generate an x-ray beam and displaced from the detector, the detector being configured to receive the x-ray beam within a first area;

a light source to generate a light beam, the light source being displaced from the detector such that the light beam produces a light field within a second area;

a radio-opaque template positioned on the detector; and a processing module configured to determine an offset distance between the radiation field and the radio-opaque template.

10. The system as in claim 9, wherein the light field generated by the light beam comprises peripheral edges.

11. The system as in claim 10, wherein the radio-opaque template comprises a plurality of features configured to be aligned with the light field.

12. The system as in claim 9, wherein the radiation field generated by the x-ray beam comprises peripheral edges imaged on the detector.

13. The system as in claim 11, wherein the processing module is configured to:

determine a distance from a detected peripheral edge of the radiation field to the peripheral edge of the light field;

determine a distance from the detected peripheral edge of the radiation field to the radio-opaque point; and determine a separation distance between the radiation field and the light field.

14. A digital detector system comprising:

a plurality of rows and columns of pixels, configured to receive an x-ray beam, the x-ray beam being detected by the rows and columns of pixels and producing image data, each pixel having circuitry for providing a signal from radiation received;

a radio-opaque template adapted to be disposed on the digital detector, the template having a plurality of radio-opaque features; and a processing module adapted to compute offset distances from peripheral edges of a radiation field and edges of a light field as indicated projections of the template features in an x-ray image of the radiation fields.

15. The digital detector system as in claim 14, wherein the radio-opaque template is aligned substantially parallel to and coincident with peripheral edges of the light field.

16. The digital detector system as in claim 14, wherein the x-ray beam produces a radiation field on the detector that is identifiable by reference to locations of the rows and columns of pixels.

17. The digital detector system as in claim 14, wherein the features include lines and point which are radio-contrasted with a substrate material.

18. The digital detector system as in claim 17, wherein the processing module is configured to:

determine a distance from a detected peripheral edge of the radiation field produced from the x-ray beam to a feature of the radio-opaque template; and determine an offset distance between the radiation field and the light field.

19. A system for aligning a imaging system comprising:

means for positioning an x-ray source configured to generate a first x-ray beam at a distance from a digital detector;

means for generating a light field in a first area on the digital detector;

means for generating an x-ray field in a second area on the digital detector;

means for identifying alignment of the light field in image data for the x-ray field; and means for computing an offset distance between the first area and the second area based upon the image data.

20. The system as in claim 19, wherein the means for identifying alignment includes a radio-opaque template.

21. The system as in claim 20, wherein the radio-opaque template comprises a plurality of radio-opaque lines and points.

22. The system as in claim 21, wherein the lines of the radio-opaque template are configured to be placed substantially parallel to and coincident with the light field.

23. The system as in claim 19, wherein the digital detector comprises a plurality of rows and a plurality of columns which define an image matrix, and wherein the image data affords measurement of the offset distance based upon positions of the rows and columns of pixels.

24. The system as in claim 19, wherein means for computing the offset distance further comprises:

means for determining a distance from features of a radio-opaque template to the peripheral edges of the x-ray field.

* * * * *